United States Patent [19]

Tagaya et al.

[11] 4,241,256
[45] Dec. 23, 1980

[54] APPARATUS FOR DETECTING FOREIGN MATTERS IN LIQUIDS

[75] Inventors: Ryosaku Tagaya, Isesaki; Tsugutoshi Sugiyama, Akishima, both of Japan

[73] Assignee: Eisai Co., Ltd., Tokyo, Japan

[21] Appl. No.: 920,622

[22] Filed: Jun. 29, 1978

[30] Foreign Application Priority Data

Jul. 29, 1977 [JP] Japan .................................. 52/91193

[51] Int. Cl.³ .............................................. H01J 40/14
[52] U.S. Cl. ................................. 250/223 B; 356/240
[58] Field of Search ............... 250/216, 223 R, 223 B, 250/234, 235, 236; 356/240

[56] References Cited

U.S. PATENT DOCUMENTS

| | | |
|---|---|---|
| 2,454,412 | 11/1948 | Stoate . |
| 3,797,632 | 3/1974 | Riggs ............................. 250/223 B |
| 3,886,353 | 5/1975 | Shioya .................................. 356/240 |
| 4,158,625 | 6/1979 | Takahashi et al. ............... 250/223 B |

*Primary Examiner*—David C. Nelms
*Attorney, Agent, or Firm*—Blanchard, Flynn, Thiel, Boutell & Tanis

[57] ABSTRACT

Apparatus for detecting foreign matters by illuminating foreign matters which swirl together with a liquid in a transparent container and measuring transmitted light. Transparent containers filled with liquid are fed one by one to the receiving seats on the transferring board which moves continuously at a fixed speed. The transparent container on the receiving seat, upon arrival at a certain position, is turned at a high speed, while being transferred continuously. Foreign matters that might be preset in liquid are caused to suspend in the liquid. The transparent container, with foreign matters suspended, is moved to the position where the optical detector is located, then the optical detector begins to move in synchronism with the transferring board. During this synchronous movement the container is illuminated by the light source in the optical detector and the light which has been transmitted through the liquid is received by the optical detector. Judgement for acceptance or reject is made according to the quantity of light received. Upon completion of the judging action, the optical detector alone is restored quickly for subsequent judging action.

11 Claims, 2 Drawing Figures

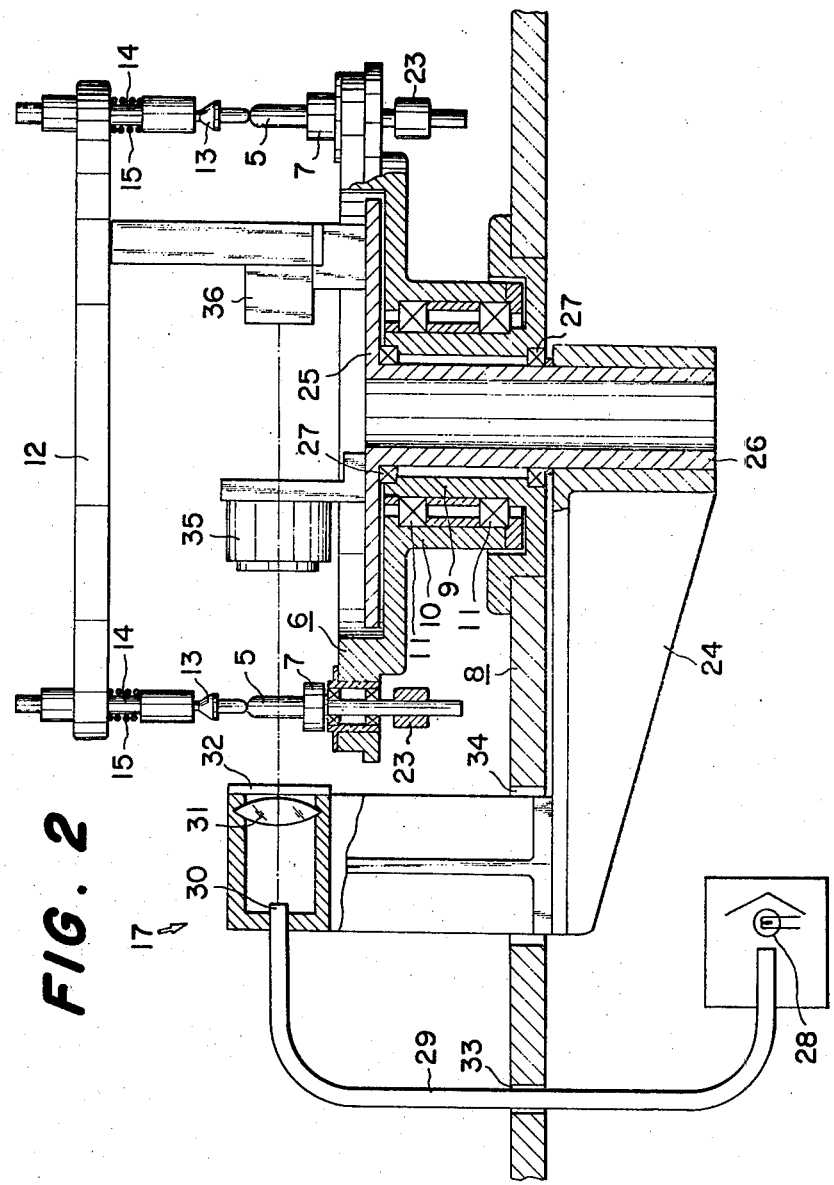

APPARATUS FOR DETECTING FOREIGN MATTERS IN LIQUIDS

BACKGROUND OF THE INVENTION

The present invention relates to an apparatus for detecting foreign matters that might be present in a liquid. More particularly, this invention relates to an apparatus for detecting stably and efficiently undesirable, minute foreign matters that might be present in medical fluids filled in transparent containers such as injection ampoules and vials.

Medical fluids in transparent containers such as injection ampoules and vials often contain such foreign matters as glass chips, granules, and fibers. The presence of such foreign matters is not desirable from a standpoint of quality, and it is necessary to reject those containers containing foreign matters by inspecting all the transparent containers filled with medical fluids.

The following method has been employed up to date for detecting the presence of minute foreign matters in medical fluids filled in transparent containers. A transparent container to be inspected is rotated at a high speed, and then brought to a standstill quickly, permitting foreign matters to suspend and swirl together with the fluid. The container is illuminated and the light which has passed through the fluid is received by an optical detector. Judgement for acceptance or rejection is made according to the degree of decrease in light received. Judgement for acceptance or rejection can also be made by measuring with an optical detector the quantity of light scattered by foreign matters in the fluid. In this method it is necessary that the transparent container to be inspected should be positioned in alignment with the optical axis of the optical detecting unit made up of a light source, lenses, and a detector. In the conventional apparatus the optical detecting unit which illuminates and receives light is unmovably mounted and the transferring board which feeds the containers continuously is mounted for intermittent rotary movement. The container to be inspected is stopped temporarily on the above-mentioned optical axis. Such temporary stopping of the container makes it necessary to move the container by mechanical action within a short time of an intermittent moving action. The transferring speed cannot be increased without sacrificing the stability of the container to be inspected. Mechanism becomes complex for stabilization of the container and the inspection capacity is low.

BRIEF SUMMARY OF THE INVENTION

The present invention has been made to overcome shortcomings associated with the conventional apparatus as mentioned above. According to the present invention, the transferring board to feed the containers to be inspected moves continuously at a fixed speed, and does not stop temporarily or change in speed. The optical inspecting unit provided adjacent to the transferring board moves over a certain distance in synchronism with the transferring board, and then restores quickly. In particular, the transferring board is circular and the containers to be inspected are moved continuously at a fixed speed around the central axis. The optical detecting unit and the transferring unit are mounted on the common shaft and they move together over a certain distance until detection is completed. Upon completion of detection, the optical detecting unit is restored quickly. This permits fast, continuous transfer, reduces detection time, and greatly improves screening efficiency. The absence of shocking action makes easy accurate synchronization with the optical detecting unit, and permits stable inspection. In addition, the structure to support the container to be inspected on the transferring board can be simplified. The uniform movement of the transferring board makes easy the connection with the means to supply containers to be inspected and with the means to discharge the inspected containers. More particularly, according to this invention a feed wheel and a discharge wheel are employed and they are easily synchronized with the transferring board.

As will be apparent from the above foregoing, it is an object of this invention to provide an apparatus that performs judgment for acceptance or rejection continuously and efficiently.

It is another object of this invention to provide an apparatus in which the container to be inspected and the optical axis coincide with each other even during rapid movement and accurate inspection is ensured.

It is further another object of this invention to provide an apparatus which is simple in structure and efficient to operate.

Other objects and advantages of this invention will become readily apparent from the following description and accompanying drawings.

BRIEF DESCRIPTION OF THE DRAWING

FIG. 2 is an enlarged cross-sectional view of the transferring board and the optical detecting unit.

DETAILED DESCRIPTION

Figure 1:
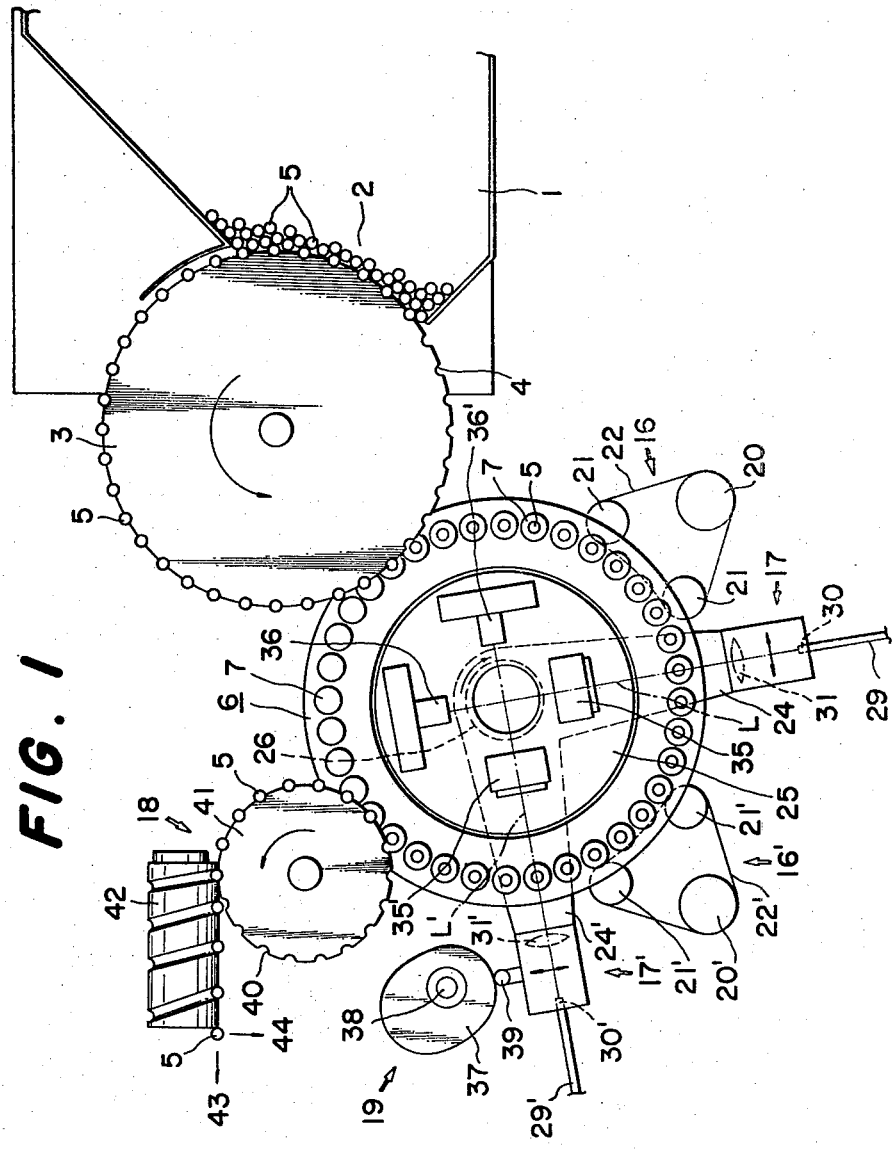
FIG. 1 is a plan view of an apparatus suitable for carrying out an embodiment of the present invention.

In FIG. 1 there is shown the feed hopper (1). The discharge opening (2) of the feed hopper (1) fronts the feed star wheel (3) that rotates in the direction of arrow continuously at a constant speed. To the periphery of the feed star wheel (3) are provided at fixed intervals a multiplicity of engaging notches (4) that catch the containers like ampoules (5) to be inspected and transfer them to the receiving seats (7) provided at the same intervals on the transferring board (6). The transferring board (6) rotates continuously like a turntable in synchronism with the feed star wheel (3). In FIG. 2 there is shown the stationary board (8), at the center of which is fixed vertically the supporting shaft (9). To the periphery of the supporting shaft (9) is rotatably fitted the inner cylinder part (10) of the transferring board (6) through the bearing (11). The transferring board (6) is driven continuously at a constant speed by a motor which is not shown in the figure. The cap mounting plate (12) which rotates together with the transferring board (6) is provided above the transferring board (6). The supporting caps (13) are provided at the same intervals as the receiving seats (7) beneath the cap mounting plate (12). The supporting cap (13) is provided on the lower end of the guide shaft (14) which slides vertically, and is forced downward by the spring (15) but is rotatable about the guide shaft (14). When the container (5) to be inspected is fed from the feed start wheel (3) to the receiving seat (7) on the transferring board (6), the cap (13) is lowered to hold the container (5).

Along the periphery of the transferring board (6) (FIG. 1) are provided the first stirring unit (16), the first detecting unit (17), the second stirring unit (16'), the second detecting unit (17'), and the selecting unit (18). The reciprocating unit (19) is provided in juxtaposition with the second detecting unit (17'). The first and second stirring units (17) (17') are made up of the motors (20) (20'), the pulleys (21) (21'), and the belts (22) (22'), respectively. The belts (22) (22') are in contact with the pulley (23) at the lower end of the receiving seat (7) so that they turn at high speeds the container (5) to be inspected. The first and second detecting units (17) (17') are mounted on the arms (24) (24') extending perpendicularly under the transferring board (6) and on the disk (25) which rotates together with the arms (24) (24'). The shaft (26) is rotatably mounted through the bearing (27) in the supporting shaft (9). To the lower end of the shaft (26) are fixed the arms (24) (24') which extend perpendicularly. On the respective arms (24) (24') are provided the light sources (30) (30') consisting of the reflector lamp (28) and the light guide (29), the projector lenses (31) (31') which parallel the light from the light sources (30) (30'), and the slit panels (32) (32') having vertical slits. The light guide passes through the arc slit (33) on the stationary board (8), and the member supporting the projection lens and slit plate projects upward through the arc slit on the stationary board (8) so that the slit plate (32) fronts the container (5) to be inspected. To the disk (25) integrally provided at the upper end of the shaft (26) are provided the focusing lenses (35) (35') and the detectors (36) (36') in alignment with the optical axes (L) (L') formed by the light sources (30) (30') and the projection lenses (31) (31'). These components constitute the first and second detecting units (17) (17').

The reciprocating unit (19) is provided in such a manner that the eccentric cam plate (37) is turned by the shaft (38) and the eccentric plate (37) oscillates the arm (24') about the shaft (26), being in contact with the guide roller (39) provided to the arm (24'). The selecting unit (18) consists of the discharge star wheel (41) having on the periphery thereof the engaging nothces (40) disposed at the same intervals as the receiving seats (7) and the screw conveyor(42) that rotates in engagement with the discharge star wheel (41). The containers which have undergone inspection are separated at the forward end of the selecting unit into the accepted products receiver (43) and the rejected products receiver (44). The reciprocating motion of the arms (24) (24') regulated by the eccentric cam plate (37) of the reciprocating unit (19) is set up as follows: It is assumed that 36 containers (5) to be inspected are held on the turntable-type transferring board (6) at intervals of radial angle of 10°. Then, it follows that the arms (24) (24') must reciprocate over a certain distance while the transferring board (6) moves over the radial angle of 10°. If the reciprocating speed is the same, the reciprocating motion is made within the radial angle of 5°. It is necessary from standpoint of stable inspection to maximize the optically stationary time or inspection time in which the transferring board (6) and the arms (24) (24') move forward in synchronism with each other. Thus it is preferable to move forward slowly and restore quickly. The eccentric cam plate (37) should of such a shape as to meet this requirement.

We will describe the action of an apparatus according to the present invention. Ampoules (5) and the like to be inspected are fed from the feed hopper (1) and caught by the engaging notches (4) of the feed star wheel (3) and then delivered to the receiving seat (7) on the turntable-type transferring board (6). The holding cap (13) comes down to hold firmly the ampoule (5). The ampoule (5) is transferred at a constant speed upon arrival at the first stirring unit (16), the ampoule comes in contact with the belt (22) and the pulley (23) that rotate the ampoule at a high speed. After passing through the first stirring unit (16), the ampoule (5) is brought to a standstill. Minute foreign matters that might be present in the ampoule continue suspended. The ampoule is transferred further to the first detecting unit (17), which is moved by the reciprocating unit (19) in synchronism with the ampoule (5) on the transferring board (6). The light source (30), lens (31), ampoule (5), focusing lens (35), and detector (36) are aligned with the optical axis (L), and during this time the inspection is carried out. Upon completion of inspection, the first detecting unit (17) is restored quickly for inspection of the subsequent ampoule (5).

The ampoule (5) which has undergone the first inspection is then subjected to the second inspection, exactly the same as the first inspection, by the second stirring unit (16') and the second detecting unit (17'). When the ampoule (5) comes to the discharge star wheel (41) after the second inspection, the holding cap (13) is raised against the force of the spring (15), and the ampoule (5) is caught by the engaging notches (40). The ampoule (5) is transferred to the screw conveyor (42). The results of the first and second inspection are calculated and stored as selecting signals in the selecting unit which is not shown. When the ampoule comes to the forward end of the screw conveyor (42), it is directed to the accepted product receiver (43) or the rejected product receiver (44) according to the selecting signals stored up to that time.

In the above-mentioned embodiment, the apparatus is so designed as to perform inspection twice, and the arms (24) (24') are designed as an L-shaped one and the first and second units (17) (17') are mounted on the straight portions of the "L". The number of inspection is not limited to twice, but it may be once or more than three times. The shape of the arm may be changed according to the number of inspections to be performed.

In the above-mentioned embodiment, the transferring board (6) is of turntable type, but it is not limited to this type; it may be one which moves linearly like an endless belt. In such a case the detecting units are so constructed as to reciprocate linearly.

In the above-mentioned embodiment, the first and second detecting units (17) (17') are so designed as to detect transmitted light, but a system to detect reflected light may be used instead.

What is claimed is:

1. An apparatus for detecting foreign matter in liquid in containers, comprising:
a transferring board on which a plurality of containers to be inspected are held at certain intervals, a means for rotating the containers abruptly in succession, said transferring board being mounted for movement continuously at a constant rate, a detecting means comprising a light source and lens and detector located along a common axis and all mounted for reciprocation together along said transferring board with said common axis having a direction of movement transverse to itself, and a reciprocating means for advancing said detecting means over a prescribed distance in synchronism with said transferring board, while detecting light from the container inspected, and subsequently retracting said detecting means more rapidly than said advancing, to the position where a succeeding container is detected.

2. The apparatus of claim 1, wherein said detecting means detects light which has passed through the object inspected.

3. The apparatus of claim 1, wherein more than two units of said detecting means are installed adjacent said transferring board.

4. The apparatus of claim 1, wherein said transferring board is a turntable that rotates at a constant speed with said light source, lens, detector and common axis of said detecting means being supported on a holder mounted for circumferential reciprocation concentrically with respect to the revolving shaft of said turntable, said reciprocating means comprising an eccentric cam plate operatively connected to said holder to reciprocate same.

5. The apparatus of claim 4, wherein said holder includes an L-shaped member and two detecting means are installed independently on arms of said L-shaped member, with said revolving shaft extending rotatably through said L-shaped member at the bend thereof joining said arms.

6. Apparatus for detecting foreign matter in liquid in containers, comprising:
- a turntable rotatable at a constant speed for circumferentially advancing the circumferential array of containers to be inspected;
- means for imparting a spin to the contents of containers;
- a detecting means having two parts, namely a light source and detector spaced along a common axis;
- outer support means mounted coaxially with said turntable for circumferential reciprocation with respect to said turntable and extending outward beyond said container array on said turntable;
- inner support means mounted coaxially with said turntable inboard of said container array and fixed with respect to said outer support means for circumferential reciprocation with said outer support means and with respect to said turntable, said outer support means carrying one said part of said detecting means radially outboard of said container array and said inner support means carrying the other said part of said detecting means radially within the container array, said common axis extending generally parallel to the plane of reciprocation of said support means across the path of circumferential advancement of said containers;
- means actuable to reciprocate said inner and outer support means for returning said light source and detector in a direction against the container advancing direction after each advancing step of said light source and detector with a container on said turntable.

7. The apparatus of claim 6, in which said outer support means comprises an arm extending radially from the rotational axis of said turntable and disposed below said turntable, said inner support means comprising a deck extending radially from the rotational axis of said turntable above said turntable and shaft means coaxially connecting said arm and deck and circumferentially reciprocable with respect to said turntable.

8. The apparatus of claim 7, in which said detector is carried by said deck on the side thereof furthest from said container to be detected and separated therefrom by the rotational axis of said turntable, said light source being carried on a member fixed to and extending upward from the radially outer free end of said arm.

9. The apparatus of claim 8 in which said detecting means further includes a focusing lens carried on said deck on the opposite side of the rotational axis of the turntable from said detector.

10. The apparatus of claim 8 including a stationary board rotatably supporting said turntable thereatop, said arm extending from the rotational axis of said turntable below said stationary board, said board having a slot therethrough through which said light source carrying member extends upward for circumferential reciprocation, said light source including a lamp disposed below said stationary board and an upstanding light guide extending from said lamp upward through a further slot in said stationary board to said light source carried atop said upstanding member.

11. The apparatus of claim 6 including a second detecting means comprising two parts, namely a light source and detector, spaced along a second common axis, said first-mentioned and second common axes crossing substantially at the rotational axis of said turntable, said outer support means being a substantially L-shaped member as seen along the turntable rotational axis and formed by a pair of said arms fixed together adjacent said turntable rotational axis for common reciprocation.

* * * * *